US012697153B2

(12) United States Patent
Medoff

(10) Patent No.: US 12,697,153 B2
(45) Date of Patent: Aug. 4, 2026

(54) BONE IMPLANT AND METHOD OF CONTROLLING THE BONE IMPLANT

(71) Applicant: TriMed, Incorporated, Santa Clarita, CA (US)

(72) Inventor: Robert Medoff, Kailua, HI (US)

(73) Assignee: TriMed, Inc., Santa Clarita, CA (US)

( * ) Notice: Subject to any disclaimer, the term of this patent is extended or adjusted under 35 U.S.C. 154(b) by 0 days.

(21) Appl. No.: 17/388,295

(22) Filed: Jul. 29, 2021

(65) Prior Publication Data

US 2023/0031466 A1 Feb. 2, 2023

(51) Int. Cl.
*A61B 17/72* (2006.01)
*A61B 17/86* (2006.01)

(52) U.S. Cl.
CPC ........ *A61B 17/7291* (2013.01); *A61B 17/863* (2013.01)

(58) Field of Classification Search
CPC . A61B 17/7291; A61B 17/7225; A61B 17/88; A61B 17/8872; A61B 17/8625; A61B 17/863; A61B 17/864; A61B 17/865; A61B 17/8685
See application file for complete search history.

(56) References Cited

U.S. PATENT DOCUMENTS

| | | | | | |
|---|---|---|---|---|---|
| 6,030,162 | A * | 2/2000 | Huebner | ............ | A61B 17/8863 |
| | | | | | 411/413 |
| 6,338,732 | B1 * | 1/2002 | Yang | .................. | A61B 17/7216 |
| | | | | | 606/62 |

| | | | | | |
|---|---|---|---|---|---|
| 8,562,606 | B2 * | 10/2013 | Richter | .............. | A61B 17/1775 |
| | | | | | 606/62 |
| 2005/0107791 | A1 * | 5/2005 | Manderson | ........ | A61B 17/7216 |
| | | | | | 606/62 |
| 2005/0277940 | A1 * | 12/2005 | Neff | .................... | A61B 17/8875 |
| | | | | | 606/310 |
| 2009/0062797 | A1 * | 3/2009 | Huebner | ............ | A61B 17/1739 |
| | | | | | 606/151 |
| 2009/0210016 | A1 * | 8/2009 | Champagne | ......... | A61B 17/863 |
| | | | | | 606/104 |

(Continued)

FOREIGN PATENT DOCUMENTS

| | | | | | |
|---|---|---|---|---|---|
| EP | | 2564799 | A1 * | 3/2013 | ......... A61B 17/7291 |
| WO | WO-2019050833 | A1 * | 3/2019 | | ......... A61B 17/7291 |

*Primary Examiner* — Eduardo C Robert
*Assistant Examiner* — Anna V. Little
(74) *Attorney, Agent, or Firm* — Wood, Phillips, Katz, Clark & Mortimer

(57) ABSTRACT

The combination of: a) an implant having a body with a leading end and a trailing end and external threads extending around a lengthwise axis, the body having an axial through passage and configured to be directed into a bone passage whereby upon turning the body in a first direction around the lengthwise axis, the external threads engage a surface bounding the bone passage and cause the implant to be advanced in an assembly direction into an operative position; and b) a removal tool with a first component that is configured to be engaged with the body with the implant in the operative position in such a manner that the body will follow movement of the first component as the first component is: a) turned in a direction opposite to the first direction; and b) drawn in a direction oppositely to the assembly direction to thereby allow the implant to be separated from the bone.

22 Claims, 6 Drawing Sheets

(56)　　　　　References Cited

U.S. PATENT DOCUMENTS

| | | | | |
|---|---|---|---|---|
| 2011/0009865 | A1* | 1/2011 | Orfaly ................ | A61B 17/7225 |
| | | | | 606/62 |
| 2013/0012942 | A1* | 1/2013 | Nelson ............... | A61B 17/7266 |
| | | | | 606/63 |
| 2013/0041414 | A1* | 2/2013 | Epperly ............. | A61B 17/7266 |
| | | | | 606/310 |
| 2013/0150903 | A1* | 6/2013 | Vincent .............. | A61B 17/8605 |
| | | | | 606/301 |
| 2014/0107714 | A1* | 4/2014 | Pech ................... | A61B 17/863 |
| | | | | 606/315 |
| 2014/0276894 | A1* | 9/2014 | Ramsay ............. | A61B 17/8897 |
| | | | | 606/104 |
| 2014/0277186 | A1* | 9/2014 | Granberry .......... | A61B 17/7291 |
| | | | | 606/301 |
| 2014/0277191 | A1* | 9/2014 | Evans ................ | A61B 17/7225 |
| | | | | 606/316 |
| 2015/0230843 | A1* | 8/2015 | Palmer ............... | A61B 17/7291 |
| | | | | 606/331 |
| 2015/0256290 | A1* | 9/2015 | Hwang ............. | H03M 13/2906 |
| | | | | 714/776 |
| 2016/0256290 | A1* | 9/2016 | Seavey .............. | A61B 17/8872 |
| 2016/0287300 | A1* | 10/2016 | Mccormick ........ | A61B 17/7291 |
| 2017/0079699 | A1* | 3/2017 | Fallin .................. | A61B 17/725 |
| 2017/0100171 | A1* | 4/2017 | Palmer ............... | A61B 17/863 |
| 2017/0112552 | A1* | 4/2017 | Sinnott ............. | A61B 17/7233 |
| 2017/0189090 | A1* | 7/2017 | Champagne ....... | A61B 17/7291 |
| 2018/0092674 | A1* | 4/2018 | McDaniel .......... | A61B 17/7291 |
| 2018/0242987 | A1* | 8/2018 | Lintula ............. | A61B 17/1775 |
| 2018/0263669 | A1* | 9/2018 | Peterson ............ | A61B 17/8605 |
| 2019/0070009 | A1* | 3/2019 | Champagne ......... | A61F 2/4225 |
| 2019/0357950 | A1* | 11/2019 | Bernstein ........... | A61B 17/8061 |
| 2021/0121209 | A1* | 4/2021 | Orbay ................... | A61B 17/72 |

* cited by examiner

| TURNING TOOL | | TURNING TOOL | |
|---|---|---|---|
| FITTING 58a | 56a | FITTING 58b | 56b |

| TURNING FITTING 48 | TRAILING END 46 | SHANK PORTION 54 | LEADING END 44 | |
|---|---|---|---|---|
| SECOND THREADED 52 LENGTH | | | FIRST THREADED 50 LENGTH | |
| BODY 42 | | | | |
| IMPLANT 40 | | | | |

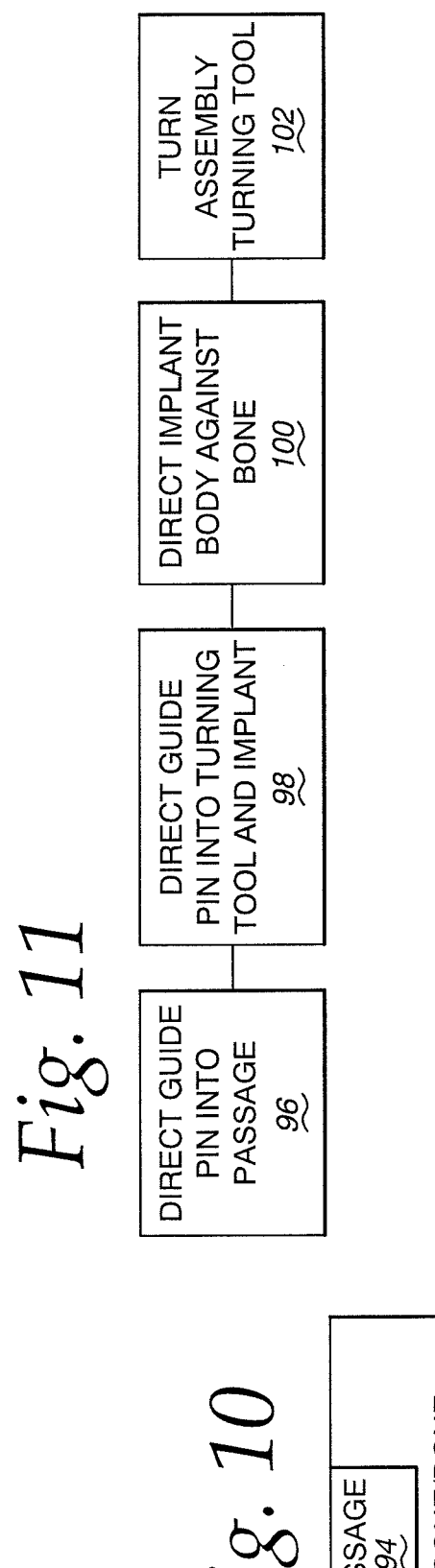
*Fig. 11*
TURN ASSEMBLY TURNING TOOL *102*
DIRECT IMPLANT BODY AGAINST BONE *100*
DIRECT GUIDE PIN INTO TURNING TOOL AND IMPLANT *98*
DIRECT GUIDE PIN INTO PASSAGE *96*
*Fig. 10*
PASSAGE *94*
BONE/BONE PART(S) *92*
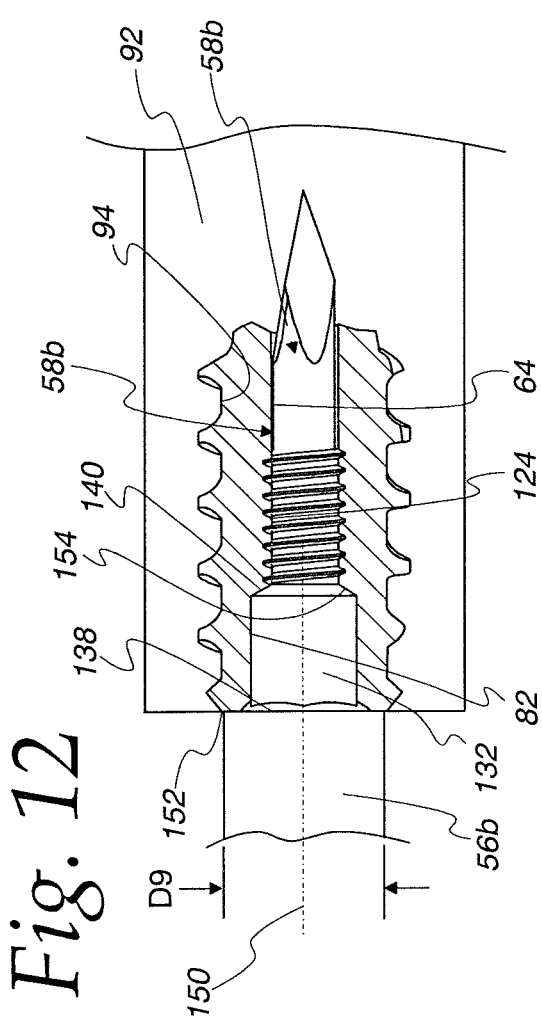
*Fig. 12*

OPERATIVELY ENGAGE FITTING
ON REMOVAL TOOL
WITH IMPLANT FITTING
*156*

TURN AND/OR DRAW
IMPLANT BODY
*158*

BONE IMPLANT AND METHOD OF CONTROLLING THE BONE IMPLANT

BACKGROUND OF THE INVENTION

Field of the Invention

This invention relates to bone treatment and, more particularly, to a threaded implant that is advanced into a bone structure to perform a fixing and/or stabilizing function.

Background Art

Threaded bone fasteners are well established as a form of fixation in orthopedic surgery. They are used to stabilize a fracture directly by inserting the fastener across a fracture site, or indirectly by inserting the fastener through a plate and into one or more bone parts. Most threaded bone fasteners have heads on their trailing end that seat on the surface of either the bone or a plate. However, one known variation is a so-called "headless bone screw", in which threads on the outer surface at the trailing end of the fastener engage a bone/bone fragment, allowing the trailing portion of the fastener to be flush with, or buried under, the surface of the bone/bone fragment.

A commonly used version of a headless bone screw utilizes a variable pitch between the leading and trailing ends of the fastener. This variation in pitch may be in the form of a leading thread section of one pitch angle (typically greater) and a trailing thread section of a different pitch angle (typically lesser). An unthreaded region is commonly located between the leading thread section and trailing thread section. The differential in pitch results in motion of two engaged bone parts towards one another as the fastener is threaded into place to produce compression at the fracture site. A variation in this design uses a pitch that gradually varies from a more coarse form to a more fine form over the length of the fastener. With either design, the trailing portion of the fastener must be configured so that the trailing pitch produces cleanly cut threads in the bone, and does not lie in thread cuts from the leading portion of the fastener that might result in thread purchase being compromised. This generally involves making the threaded trailing end of the fastener with a larger diameter root that necessitates a larger opening in the bone at the insertion site.

One method of approaching fixation across a fracture of a tubular bone in the hand or foot, such as the metacarpal, metatarsal, or phalangeal bones, is to place a pin or threaded implant down the center of the medullary canal. With this method of fixation, the pin or threaded implant acts like an intramedullary nail and lies centrally in a preferred position in the bone to resist angular torque across the bone. However, one problem with this method is that the end of the bone is capped with an articular surface of joint cartilage, and the only feasible method of placement of such an implant is to drill directly through the joint and the cartilage. Articular cartilage does not regenerate and thus minimizing damage thereto is critical. Since an intramedullary implant provides better fixation if it fills the canal, the surgeon is faced with the competing objectives of trying to get an implant large enough to provide angular stability in the canal while minimizing the damage to the articular surface during insertion.

Threaded implant placement is commonly facilitated by introducing a guide pin along which the implant is controllably advanced. This necessitates a cannulated construction for both the implant and the tool that is used to turn, and thereby advance or withdraw, the implant. Thus designers of these types of implants must also contend with the problem of maintaining the integrity of small diameter threaded implants, and tips/fittings on tools that are used to apply a torque to these implants. Reducing implant size creates the challenge of keeping the implants and tools intact as the implants are turned by the tools to effect both placement and removal of the implants, which challenge is increased by the fact that the implant and tool are both cannulated.

The above problems are further compounded in the case of the hand and foot bones because of the small diameter of the tubular bones at these sites. Commonly, these procedures involve initial placement of a guide pin down the center of the bone, drilling to the diameter of the thread roots, and then inserting the implant with an appropriate turning tool. Minimizing of damage to the articular cartilage during insertion is key. This must be achieved while using a guide pin that is stiff enough so that it does not tend to wander during the initial insertion across the fracture site.

In the metacarpal, metatarsal, or phalanges of the hand/foot, it is desirable to have a guide pin no smaller than 0.8 mm. A 3.0 mm threaded implant (outer diameter of leading thread) would use a 2.3 mm drill for the root diameter of the threads (about 2.2 mm); this would leave a fastener wall thickness of only approximately 0.7 mm. The wall thickness of the tip of the turning tool would be even smaller if the implant's size was maintained throughout the length of the implant. For this reason, standard 3.0 mm threaded implants have a larger head diameter, to allow the trailing thread to engage (as most are differential pitch), as well as to have enough wall thickness in the driving tool fitting to keep it from shearing off during insertion. In addition, turning tools for this type of implant have a shaft that is wider than the tip of the tool and the core diameter of the implant.

If an implant of this type is inserted through the joint cartilage in order to place the fastener centrally down a tubular bone of the hand or foot, the wider trailing fastener "head" and wider tool shaft may necessitate a relatively large hole that may create significant articular damage to the joint surface. This can lead to arthritis, pain, and joint dysfunction. "Headless" implants may be constructed to reduce joint cartilage damage but make the head region of the implant, and the cooperating turning tool, smaller in dimension and thus more prone to failure. This condition is aggravated by the fact that implants within medullary canals tend to bend to follow bone contour and may thus be more resistant to turning, which necessitates larger operating torque application through a turning tool.

A further problem is encountered with the above types of implants when withdrawal thereof is required. Threaded implants directed into small medullary canals tend to resist turning, particularly in small curved bones within which a relatively flexible threaded implant tends to conformingly bend. Drills used to form the implant volume, by reason of their small diameter, tend to bend to follow the contours of the medullary canals and thus do not alleviate this problem. The result is that a relatively large torque may have to be applied to the implant to effect removal, which may result in failure of the implant and/or the turning tool.

One manner of addressing the above problem is to reduce thread size. While potentially reducing required driving torque, the tenacity of the engagement between the implant and bone may be significantly reduced. A shallower and/or narrower thread configuration could also result in a compromised, or lost, bone purchase. When removal of the implant is required, reverse turning of the implant by an engaged turning tool may be ineffective in backing the implant out of the medullary canal. Rather, the implant may simply turn without any lengthwise movement resulting. The situation is made worse by the fact that medullary canals may have a nonuniform diameter. That is, commonly small diameter medullary canals, as in foot and hand bones, have an "hourglass"-shaped canal. As a result, thread purchase may be at spaced locations with only a small length of significant purchase at each such location. The implant ends often are loosely engaged to effectively float within the medullary canal. This, together with the curved shape commonly assumed by the implant when placed, may result in the requirement of manipulating the implant by other than simply turning the same, and thereby relying on thread interaction to effect its withdrawal. Such procedures may cause damage to the bone.

SUMMARY OF THE INVENTION

In one form, the invention is directed to a method of controlling an implant with respect to a bone. The method includes the steps of: obtaining an implant having a body with a lengthwise axis, the body having a leading end and a trailing end and external threads extending around the lengthwise axis; directing the implant into a passage in the bone and turning the body in a first direction around the lengthwise axis to thereby cause the external threads to engage a bone surface bounding the bone passage so as to cause the implant to advance in a first direction relative to the bone into an operative position; obtaining a removal tool having a first fitting; with the implant in the operative position, operatively engaging the first fitting with a cooperating fitting on the body at or adjacent to the trailing end so that the first fitting can be moved to thereby: a) turn the body in a second direction around the lengthwise axis that is opposite to the first direction; and b) draw the body oppositely to the first direction; and with the implant in the operative position and the first fitting engaging the cooperating fitting on the body, controlling the removal tool to at least one of: a) turn the body in the second direction; and b) draw the body oppositely to the first direction to thereby withdraw the implant from its operative position.

In one form, the implant has an axial through passage between the leading and trailing ends of the body.

In one form, the passage in the bone is a medullary canal. The step of directing the implant into the passage involves directing a guide pin into the medullary canal, engaging the body with the guide pin so that the guide pin extends into the axial through passage on the implant, and guiding the body along the guide pin.

In one form, the first fitting has threads that engage threads on the cooperating fitting on the body. The external threads and the threads on the first fitting are opposite-handed.

In one form, the external threads have first and second threaded lengths. The body has an unthreaded shank portion between the first and second threaded lengths.

In one form, the first and second threaded lengths each has threads with a pitch. The pitch of the threads on the first threaded length is substantially the same as the pitch of the threads on the second threaded length.

In one form, the first and second threaded lengths each has threads with a pitch. The pitch of the threads on the first threaded length is different from the pitch of the threads on the second threaded length.

In one form, the step of turning the body involves turning the body through a second fitting on an assembly tool with the second fitting engaged with the body. The second fitting has an axis that aligns with the lengthwise axis of the body with the second fitting engaged with the body. The body and second fitting are configured so that with the second fitting engaged with the body the second fitting and body overlap axially relative to the second fitting axis and lengthwise body axis.

In one form, the second fitting has a peripheral surface extending around the axis of the second fitting. The body of the implant has an unthreaded shank portion with a diameter. An axial length of the peripheral surface of the second fitting extends away from the body with the second fitting engaged with the body and has a diameter less than or equal to the diameter of the unthreaded shank portion.

In one form, the second fitting has a peripheral surface extending around the axis of the second fitting. The trailing end of the implant has an outer diameter. An axial length of the peripheral surface of the second fitting extends away from the body with the second fitting engaged with the body and has a diameter less than or equal to the outer diameter of the trailing end of the body.

In one form, the bone passage is a medullary canal. The bone has articular cartilage with a thickness thereon. The step of directing the implant into the bone passage involves directing the implant through the thickness of the articular cartilage. The axial length of the peripheral surface of the second fitting is at least equal to the thickness of the articular cartilage.

In one form, the first threaded length has a root with a diameter and first threads with a crest diameter. The second threaded length has a root with a diameter and second threads with a crest diameter. At least a portion of the second threads has a crest diameter greater than a crest diameter of at least a portion of the first threads.

In one form, the second fitting has a peripheral surface extending around the axis of the second fitting. The external threads extend from a root portion with a diameter. A part of the second fitting that is axially overlapped with the body has a diameter that is less than or equal to the diameter of the root portion.

In one form, the body has an axially extending receptacle into which the second fitting is directed with the second fitting engaged with the body.

In one form, the first fitting has threads that engage threads on the body. The threads on the body extend axially towards the leading end of the body to beyond the axially extending receptacle.

In one form, the axially extending receptacle has a diameter that is greater than a diameter of a portion of the through passage that is surrounded by the threads on the body that engage the threads on the first fitting.

In one form, the removal tool has a leading end. A graspable handle spaced from the leading end can be engaged to turn the removal tool and the first fitting. The removal tool has a tapered guide portion that extends to beyond the threads on the first fitting towards the leading end.

In one form, the removal tool has a stepped diameter region adjacent a leading end of the removal tool with a first diameter portion on which the threads on the first fitting are located and a second diameter portion that projects into the axially extending receptacle.

In one form, the stepped diameter region has an annular shoulder which abuts to the trailing end of the body with the first fitting engaged with the body.

In one form, the bone is one of a metacarpal, metatarsal, and phalangeal bone on one of a foot or hand.

In one form, the invention is directed to a method of controlling an implant with respect to a bone. The method includes the steps of: obtaining an implant having a body with a lengthwise axis, the body having a leading end and a trailing end and external threads extending around the lengthwise axis; obtaining a tool with a fitting; engaging the tool fitting with a cooperating fitting on the body at or adjacent to the trailing end of the body so that the tool fitting can be moved to turn the body around the lengthwise axis; and with the tool fitting engaged with the cooperating fitting, moving the tool fitting selectively to cause the body to turn in either: a) one direction around the lengthwise axis to cause the external threads to engage a bone surface surrounding a passage in the bone to thereby advance the implant in a first direction relative to the bone towards an operative position; or b) a direction opposite to the one direction to cause the implant, extended at least partially into the passage, to cause the implant to move oppositely to the first direction relative to the bone as an incident of the external threads and the bone surface surrounding the passage engaging. With the tool fitting engaged with the cooperating fitting, an axial length of the tool fitting extends away from the body and has a peripheral surface with a diameter that is less than or equal to an outer diameter of the trailing end of the body.

In one form, the body of the implant has an unthreaded shank portion with a diameter. The diameter of the peripheral surface of the axial length of the tool fitting is less than or equal to the diameter of the unthreaded shank portion.

In one form, the passage in the bone is a medullary canal.

In one form, the bone has articular cartilage with a thickness thereon. The method further includes the steps of directing the implant through the articular cartilage and into the bone passage and advancing the implant in the first direction into the operative position. With the implant in the operative position, the axial length of the tool fitting extending away from the body is at least equal to the thickness of the articular cartilage.

In one form, the implant has an axial through passage between the leading and trailing ends of the body.

In one form, the passage in the bone is a medullary canal. The method further includes the steps of: directing a guide pin into the medullary canal; engaging the body with the guide pin so that the guide pin extends into the axial through passage in the implant; and guiding the body along the guide pin.

In one form, with the implant in the operative position the axial length of the tool fitting extending away from the body is greater than the thickness of the articular cartilage.

In one form, the bone has an external surface through which the passage is formed. With the implant in the operative position, the trailing end of the body is recessed below the external surface of the bone.

In one form, the cooperating fitting has an axially extending receptacle into which the tool fitting is directed with the tool fitting engaged with the cooperating fitting.

In one form, the bone is one of a metacarpal, metatarsal, and phalangeal bone in one of a foot or hand.

In one form, the external threads have a threaded length at the trailing end of the body with a root. The diameter of the peripheral surface of the axial length of the tool fitting is less than or equal to a diameter of the root.

In one form, the invention is directed to the combination of an implant and a removal tool. The implant has a body with a lengthwise axis. The body has a leading end and a trailing end and external threads extending around the lengthwise axis. The body has an axial through passage between the leading and trailing ends of the body. The body is configured to be directed into a bone passage whereby upon turning the body in a first direction around the lengthwise axis, the external threads engage a bone surface bounding a passage into which the implant is directed in an assembly direction to advance the implant into an operative position. The removal tool has a first fitting that is configured to be engaged with the body with the implant in the operative position in such a manner that the body will follow movement of the first fitting as the first fitting is: a) turned in a direction opposite to the first direction; and b) drawn in a direction oppositely to the assembly direction to thereby allow the implant to be separated from the bone.

In one form, the invention is directed to the combination of an implant having a body with a lengthwise axis and a tool for turning the body around the axis. The body has a leading end and a trailing end and external threads extending around the lengthwise axis. The body has an axial through passage between the leading and trailing ends of the body. The body is configured to be directed into a bone passage whereby upon turning the body in a first direction around the lengthwise axis, the external threads engage a bone surface bounding a passage into which the implant is directed in an assembly direction to advance the implant into an operative position. The body has a shank portion with a diameter. The tool has a fitting that engages the body such that the fitting is in axially overlapping relationship with the body. The fitting has a diameter that is less than or equal to the diameter of the body shank portion. The fitting on the tool and implant are configured so that with the fitting engaged with the body, the body will follow movement of the fitting around the lengthwise axis to cause the implant to be advanced through the bone passage and into an operative position.

In one form, with the fitting engaged with the body the fitting overlaps the body over a first axial length. The filling has an axial length extending away from the body that is at least equal to the first axial length. The fitting has a diameter that is less than or equal to the diameter of the body shank portion.

In one form, with the fitting engaged with the body, the fitting overlaps the body over a first axial length. The fitting has an axial length: a) extending away from the body that is at least equal to the first axial length; and b) having a diameter that is less than or equal to a diameter of the at least one root.

In one form, with the fitting engaged with the body, the fitting overlaps the body over a first axial length. The fitting has an axial length: a) extending away from the body that is at least equal to the first axial length; and b) having a diameter that is less than or equal to a diameter of each of the at least one root.

BRIEF DESCRIPTION OF THE DRAWINGS

FIG. 10 is a schematic representation of a bone/bone part with a passage into which the inventive threaded implant can be directed to be placed in an operative position;

FIG. 11 is a flow diagram representation of a method of controlling a bone implant, according to the invention;

FIG. 12 is a view as in FIG. 9 with a fitting on the other turning tool, as shown in FIG. 3, engaged with a fitting on the implant to facilitate movement of the threaded implant out of its operative position;

DETAILED DESCRIPTION OF THE PREFERRED EMBODIMENT

Figure 1:
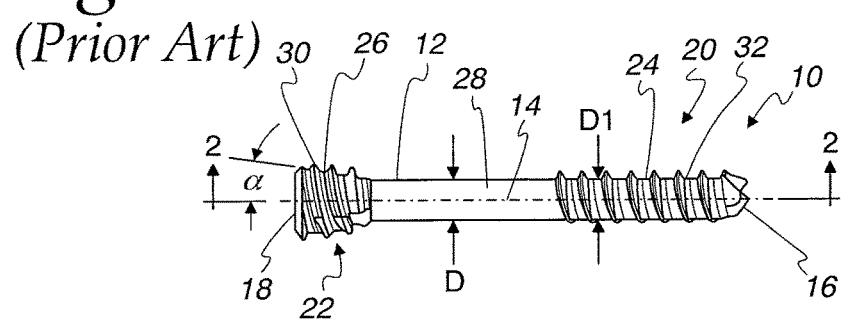
FIG. 1 is a side elevation view of a prior art fastener used to fix and/or stabilize a bone structure.
Figure 2:
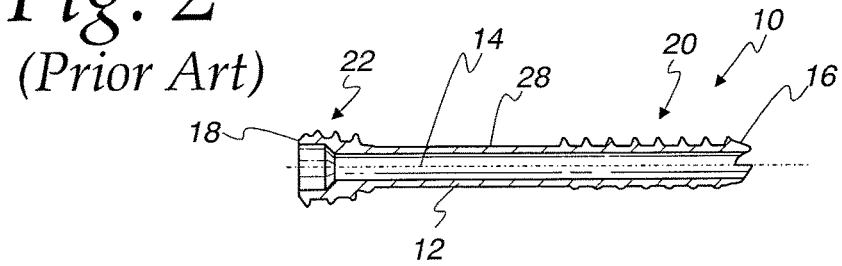
FIG. 2 is a cross-sectional view of the fastener taken along line 2-2 of FIG. 1.

In the Background Art section herein, there is description of a conventional threaded implant with axially spaced first and second threaded lengths. In FIGS. 1 and 2, one specific form of such implant, currently being offered commercially by the Applicant, is shown at 10.

The implant 10 has a cannulated body 12 with an axis 14 and a length between axially spaced leading and trailing ends 16, 18, respectively.

The implant 10 has first and second threaded lengths 20, 22.

The threaded length 20 has a root 24 with a substantially constant diameter over its length. The second threaded length 22 has a corresponding root 26 with an outer surface that is at an angle α with respect to the axis 14. In one form, the angle α is on the order of 13°, but may be 0°.

A shank portion 28 resides between the first and second threaded lengths 20, 22. The shank portion 28 has a diameter D that is substantially equal to the diameter D1 of the root 24 over the first threaded length 20.

This particular implant 10 is contemplated for use generally as a "headless" compression fastener for fracture fixation. This implant 10 is designed to be inserted through a passage formed in/across a bone. The second threaded length 22, by reason of threads 30 thereon extending to the trailing end 18, is designed to be embedded to at least a flush relationship with an exposed bone surface through which the implant 10 is directed. Alternatively, the trailing end 18 may be recessed below that surface. In either event, no part of the implant 10 is contemplated to be protruding appreciably from the bone surface after complete insertion is effected.

This particular implant 10 uses a different pitch for the threads 30 on the second thread length 22 than that for the threads 32 on the first thread length 20. By making the pitch of the threads 32 greater than that for the threads 30, as the implant 10 is inserted, the bone parts, as across a fracture site, are drawn towards each other. To allow this to occur, the threads 30 are of greater diameter to allow them to gain purchase around a bore portion through which the threads 32 have already advanced.

Consequently, any preformed passage for the implant 10, dimensioned to accept the body diameter D, must be enlarged to accommodate the root 26 and larger diameter threads 30 at the trailing end 18, whereby the aforementioned problems associated with articular surface damage are contended with, with that particular application.

Figure 3:
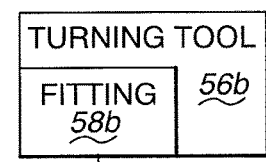
FIG. 3 is a schematic representation of a threaded implant, according to the present invention, and alternative forms of turning tool usable to place the implant in an operative position in a bone structure and separate the implant from its operative position.
Figure 3:
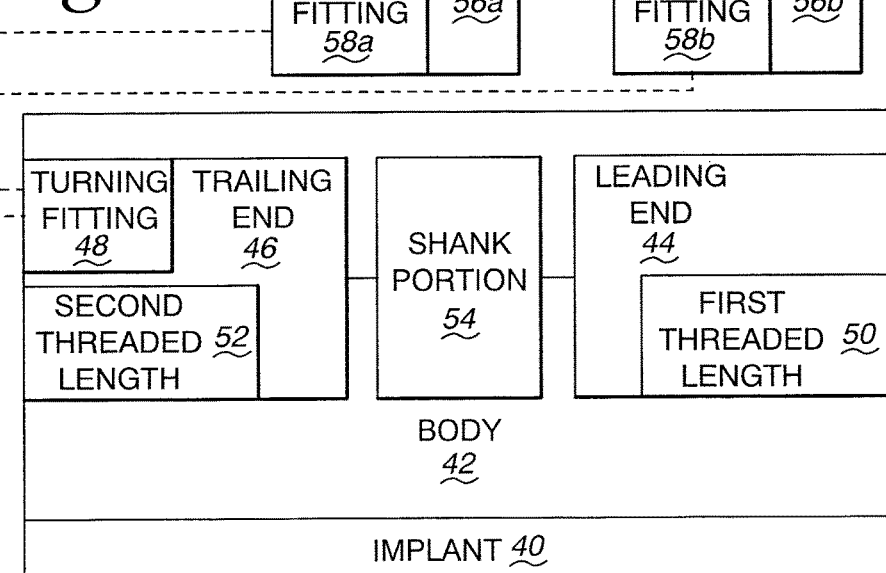

The present invention is concerned with a particular implant 40, as shown in schematic form in FIG. 3, and a method of controlling the implant 40 with respect to a bone, as to perform a fixation and/or stabilizing function thereon.

The inventive implant 40 has a body 42 with an axis and a length between axially spaced leading and trailing ends, 44, 46, respectively. The implant 40 has a turning fitting 48 at the trailing end 46.

The implant 40 has axially spaced first and second threaded lengths 50, 52, respectively at the leading end 44 and trailing end 46. A shank portion 54 is provided between the first and second threaded lengths 50, 52. The shank portion 54 may be threaded or unthreaded, but will be described in forms hereinbelow as unthreaded.

The threaded lengths 50, 52 each has a root diameter and threads with a crest diameter. In one preferred form, the root diameters of the first and second threaded lengths 50, 52 are not significantly greater than the diameter of the shank portion 54.

A turning tool 56*a* has a fitting 58*a* that is configured to make keyed connection with the implant turning fitting 48 whereby the fitting 58*a* can be turned in at least one direction around the axis of the body 42 to cause the body 42 to follow this turning movement in a tightening direction that moves the body 42 in an assembly direction, leading end first.

A separate turning tool 56*b* has a fitting 58*b* that is configured to be engaged with the turning fitting 48 in such a manner that with the fitting 58*b* engaged with the turning fitting 48, the body 42 will follow movement of the fitting 58*b* as the fitting 58*b* is: a) turned oppositely to the one direction effected through the turning tool 56*a* to advance the implant body 42; and b) drawn in a direction oppositely to the assembly direction to thereby allow the implant 40 to be backed out of, and separated from, bone into which it was previously directed.

It is possible that the turning tools 56*a*, 56*b* could be the same instrument. However, for purposes of clarity, the turning tool 56*a* will be identified as an assembly tool, whereas the turning tool 56*b* will be identified as a removal tool.

Within the generic showing of the implant 40 in FIG. 3, it is contemplated that the pitch on threads on the first and second threaded lengths 50, 52 may be the same or different. In the latter case, the implant 40 performs to produce compression between separate bone portions as described in the Background Art section herein.

Exemplary forms of the implant 40, and how it is controlled, will now be described with respect to FIGS. 4-15. In the depicted embodiment, threads 60 on the first threaded length 50 have a pitch that is the same as threads 62 on the second threaded length 52. The shank portion 54 between the threaded lengths 50, 52 is unthreaded. However, as noted above, it is contemplated that threads could extend continuously from the leading end 44 of the body 42 to the trailing end 46 thereof.

Figures 6, 7:
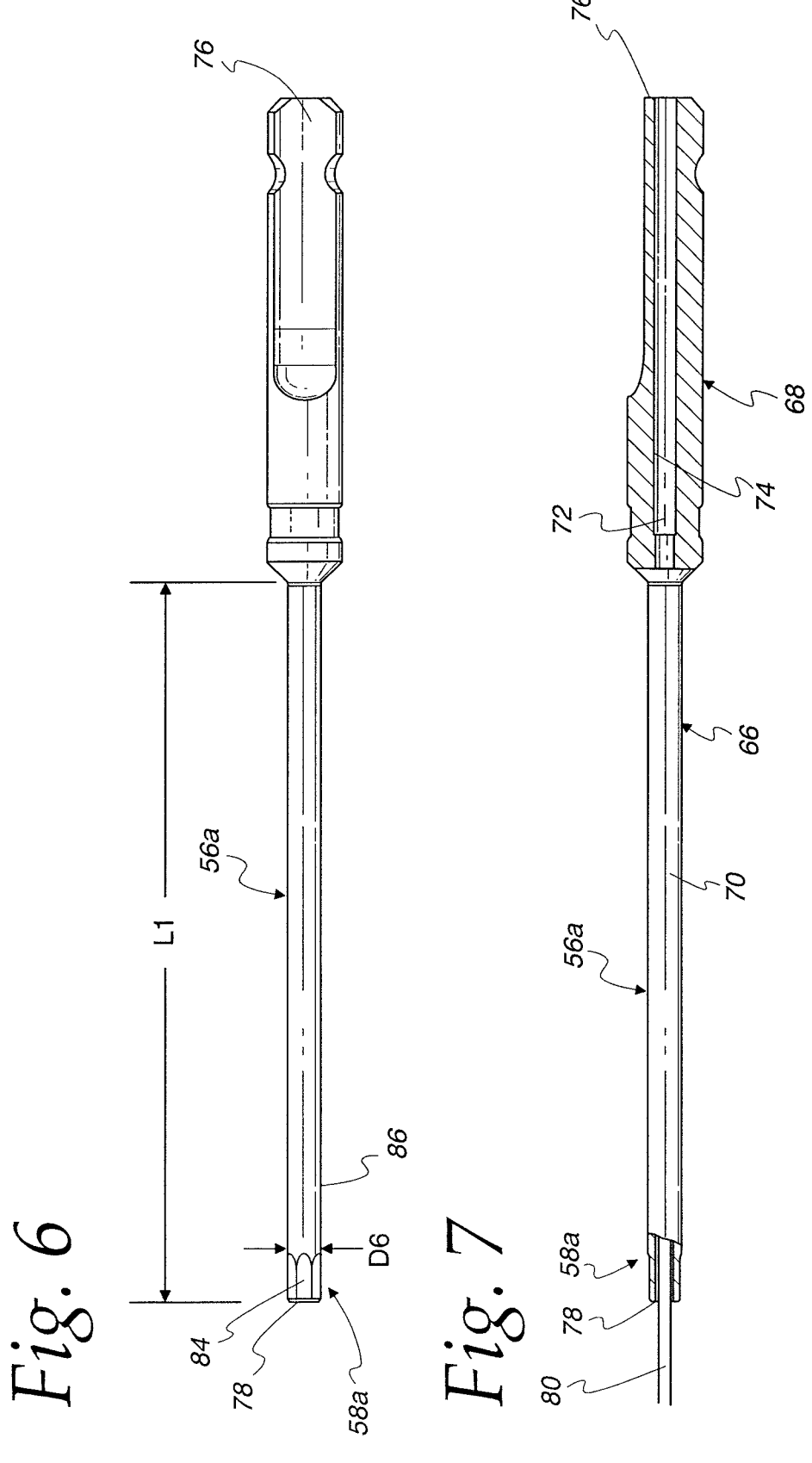
FIG. 6 is a side elevation view of one of the turning tools as shown schematically in FIG. 3 and usable to at least direct the inventive threaded implant into its operative position in bone.
FIG. 7 is a view of the tool as in FIG. 6, turned through 90° about a lengthwise axis and with portions thereof broken away.
Figure 8:
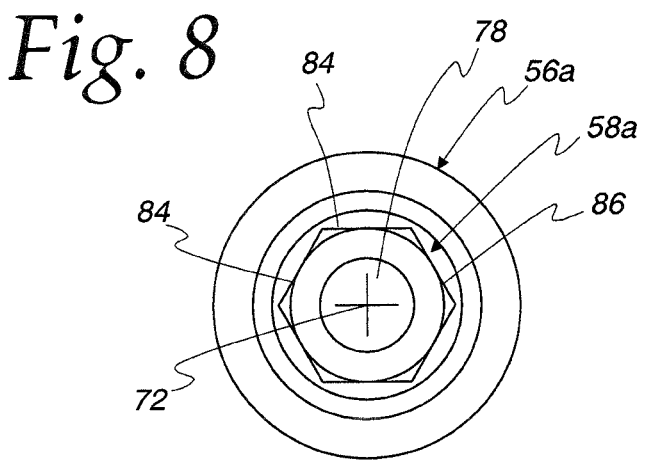
FIG. 8 is an enlarged, end elevation view of the tool in FIGS. 6 and 7.

Initially, the implant 40 will be described as engaged with the assembly turning tool 56*a*, as shown in FIGS. 6-8. The body 42 of the implant 40 and assembly turning tool 56*a* have a cannulated construction. The body 42 has an axial through passage 64. The assembly turning tool 56*a* has a body 66 consisting of a graspable handle 68 and an operating shaft 70 that projects from the handle 68 and defines the fitting 58*a* at its free end. The depicted "handle" 68 may alternatively function as a coupling to engage another element (not shown) that is graspable. The body 66 has a lengthwise axis 72 and a passage 74 extending at least partially through the lengthwise extent of the body 66. As depicted, the passage 74 extends fully axially between an end 76 of the handle 68 and a free end 78 of the operating shaft 70 defined by the fitting 58*a*.

Figures 4, 5:
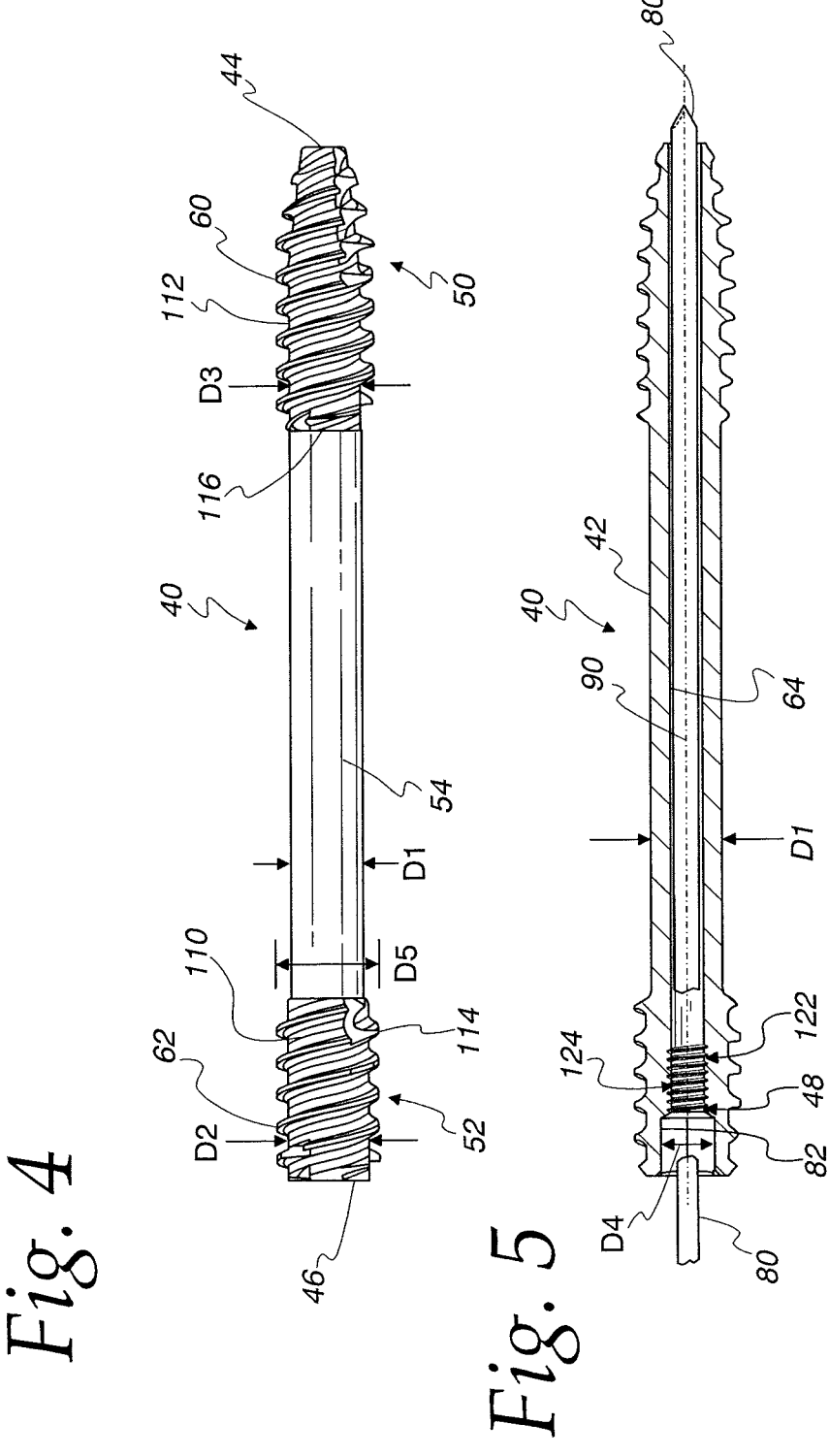
FIG. 4 is a side elevation view of one form of threaded implant, as shown in schematic form in FIG. 3.
FIG. 5 is a cross-sectional view of the threaded implant taken along line 5-5 of FIG. 4.

The through passage 64 and the passage 74 each has a diameter adequate to slidably engage a conventional type guide pin 80, as seen in FIG. 5, whereby with the guide pin 80 initially operatively situated, each of the body 42 of the implant 40 and body 66 of the assembly turning tool 56*a* can be slid thereover and move guidingly lengthwise therealong.

Figure 9:
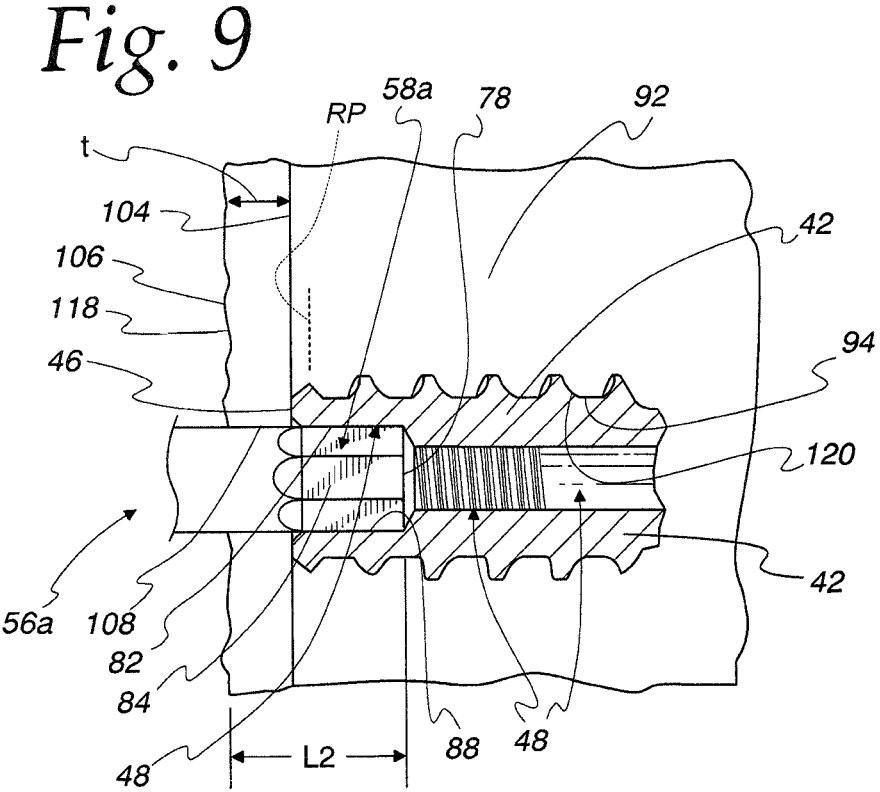
FIG. 9 is a fragmentary, cross-sectional view of a trailing end of the threaded implant with a fitting engaged with a fitting on the turning tool in FIGS. 6-8.

The turning fitting 48 on the body 42 consists of an axially extending receptacle 82 into which the leading end 78 of the fitting 58*a* on the assembly turning tool 56*a* is directed with the fitting 58*a* on the assembly turning tool 56*a* engaged with the body 42, as shown in FIG. 9.

In this embodiment, the turning tool fitting 58*a* has a plurality of flats 84 formed on a peripheral surface 86 thereof to collectively define a polygonal shape as viewed along the axis 72.

The receptacle 82 is bounded by a surface 88 with a shape complementary to that on the peripheral surface 86 on the assembly turning tool fitting 58*a* whereat the flats 84 are located. With the assembly turning tool fitting 58*a* engaged with the turning fitting 48 on the body 42, the fittings 48, 58*a* are in axially overlapping relationship and cooperate to make a keyed connection whereby turning of the fitting 58*a*, as by grasping and manipulating the handle 68, causes the body 42 to follow turning movement thereof.

There is no particular limitation as to how the cooperating fittings on the body 42 and assembly turning tool 58*a* may be configured. The depicted form is exemplary in nature only and is such that that the axis 72 of the passage 74 is coincident with the lengthwise axis 90 of the body 42 and the through passage 64 with the assembly turning tool fitting 58*a* engaged with the body 42.

The depicted construction allows the assembly turning tool 58*a* to be turned in opposite directions around the axis 72 with the fitting 58*a* engaged with the body 42. Turning of the fitting 58*a* in a first direction causes the threads 60, 62 on the body 42 to cooperate with a bone surface to advance the implant 40, leading end 44 first. Opposite turning causes the threads 60, 62 to cooperate with a bone surface to retract the implant 40 by movement in a direction, trailing end 46 first.

As shown schematically in FIG. 10, the implant 40 can be used in association with any bone/bone part(s) 92. The bone/bone part(s) 92 has a passage 94 therein that can be pre-formed, naturally formed, or formed by the implant 40 as it is advanced. As an example, the passage 94 may be produced through a boring tool. Alternatively, the passage 94 may be a medullary canal which may be altered or unaltered to accept the implant 40. As a further alternative, the passage 94 may be formed by directing the leading end 44 of the implant 40 to against the bone/bone part(s) 92 and turning the body 42 to cause the threads 60, 62 to engage the bone/bone part(s) 92 around the passage 94, whereby the implant 40 advances and progressively forms a passage 94 to accept the body 42.

In a typical method, as shown in flow diagram form in FIG. 11, the guide pin 80, as described above, is directed into a bone passage 94, as shown at block 96. As noted previously, the use of a guide pin 80 is not required.

As shown at block 98, the guide pin 80 is directed into the through passage 64 on the body 42 and the passage 74 on the assembly turning tool 56*a*.

As shown at block 100, the leading end 44 of the implant body 42 can be guided slidingly over the guide pin 80 to against bone at which the passage 94 is formed, or to be formed.

As shown at block 102, with the turning tool fitting 58*a* engaged with the body 42, the assembly turning tool 56*a* is manipulated to turn the fitting 58*a* in a first direction around the axes 72, 90, which causes the threads 60 at the leading end 44 of the body 42 to purchase bone at the surface surrounding the passage 94 to progressively advance the body 42 of the implant, leading end 44 first, into the bone.

As shown in FIG. 9, the advancing movement of the implant body 42 may place the trailing end 46 either flush with or below an exposed surface 104 of the bone/bone part 92 through which surface 104 the leading end 44 of the implant body 42 is initially directed. The latter, recessed position is indicated by the dotted line RP.

As shown in FIG. 9, a site at which the implant 40 might be used is at a joint whereat there is a layer of articular cartilage 106 with a thickness t.

To minimize damage to the articular cartilage 106, it is desirable to minimize the size of the opening 108 formed therethrough by the implant body 42 and the assembly turning tool 56*a*.

In this embodiment, the body 42 is constructed so that the shank portion 54 has a substantially uniform diameter D1 between the first and second threaded lengths 50, 52.

In this embodiment, the second thread length 52 has a root 110 which has a substantially constant diameter D2 only slightly greater than the diameter D1. Alternatively, D2 might be equal to D1.

The first threaded length 50 has a root 112 with a diameter D3, approximately equal to the diameter D2 at the trailing end 46, and substantially constant over its length and tapering adjacent the leading end 44 of the body 42.

The diameter D4 of the receptacle 82 is less than the diameter D1.

While not critical, the threads 62 extend to a crest 114 with a diameter D5 on the order of 4 mm. The pitch of the threads 62 in an exemplary form is on the order of 1.24 mm and typically changes with diameter.

A trailing region of the threads 60 may have the same size and pitch as the threads 62. The threads 60 taper in crest diameter towards the leading end 44 of the body 42.

In one preferred form, the assembly turning tool fitting 58*a* has a diameter D6 over the entire extent of the operating shaft 70 identified by the dimension L1, as shown in FIG. 6. In other preferred forms, the diameter D6 extends over at least a portion of the length of the operating shaft 70 sufficiently to allow the trailing end of the implant body 42 to be buried below the penetrated bone surface without causing the entry opening to increase in size. The diameter D6 may be equal to, or slightly less than, the diameter D4 of the receptacle 82.

Dimensions for different exemplary forms of the implant body 42 and the cooperating turning tool fitting 58*a* on the assembly turning tool 56*a* are set forth below. These forms should not be viewed as limiting and are presented only as representative forms, identified using mm dimensions.

| Form #1 | Form #2 | Form #3 | Form #4 | Form #5 |
|---|---|---|---|---|
| D1 = 1.78 | D1 = 2.06 | D1 = 2.36 | D1 = 2.69 | D1 = 2.97 |
| D2 = 2.46 | D2 = 2.79 | D2 = 3.05 | D2 = 3.05 | D2 = 3.51 |
| D4 = 2.16 | D4 = 2.41 | D4 = 2.67 | D4 = 2.67 | D4 = 3.18 |
| D2 − D4 = 0.30 | D2 − D4 = 0.38 | D2 − D4 = 0.38 | D2 − D4 = 0.38 | D2 − D4 = 0.33 |
| D4 − D1 = 0.38 | D4 − D1 = 0.35 | D4 − D1 = 0.31 | D4 − D1 = −0.02 | D4 − D1 = 0.21 |

In a generic sense, in one preferred form, the diameter D6 is less than or equal to the largest core diameter of the body 42, whereby the turning tool will not enlarge the opening produced by the implant body 42 through the bone and any overlying soft tissue.

It is preferred that the diameter D6 be maintained, or not significantly increased, over at least a length dimension L2 in FIG. 9 equal to a distance from the end 78 to the outer surface 118 of the articular cartilage 106 with the assembly turning tool fitting 58a engaged with the body 42 as shown in FIG. 9 at the intended depth of insertion of the implant body 42.

Accordingly, since the diameter D6 is equal to or less than the diameter D2 of the root portion along the threaded length 52, no part of the assembly turning tool fitting 58a will enlarge the opening 108 through the articular cartilage 106 beyond that dimension produced by the passage of the threaded length 52, and particularly the diameter of the shank portion 54 and the diameters of the roots 110, 112 associated with the threaded lengths 52, 50, respectively.

When it is desired to withdraw the implant 40 from its operative position, as shown in FIG. 9, the assembly turning tool 56a can be utilized by engaging the fitting 58a with the body 42, as shown in FIG. 9, and turning the fitting 58a through the turning tool 56a oppositely to the aforementioned first direction to thereby cause the threads 60, 62 to cooperate with the bone surface 88 so as to cause the implant 40 to move trailing end 46 first out of the passage 94.

However, as noted above, the threads 60, 62 may not maintain adequate purchase with a surface 120 surrounding the passage 94, whereby simply turning the implant body 42 around its axis 90 in the second direction may not permit extraction of the implant 40 from the passage 94. The compromised thread engagement may be a result of the geometry of the passage 94, particularly when a medullary canal defines the passage 94. Stripping of the bone may occur as the implant is initially placed in the operative position or over time as the bone is subjected to forces through normal human movement. Typically, when bone threads have been compromised, time-consuming extraction procedures may be required that may damage the bone and complicate further repair and/or stabilization.

Figures 13, 14, 15:
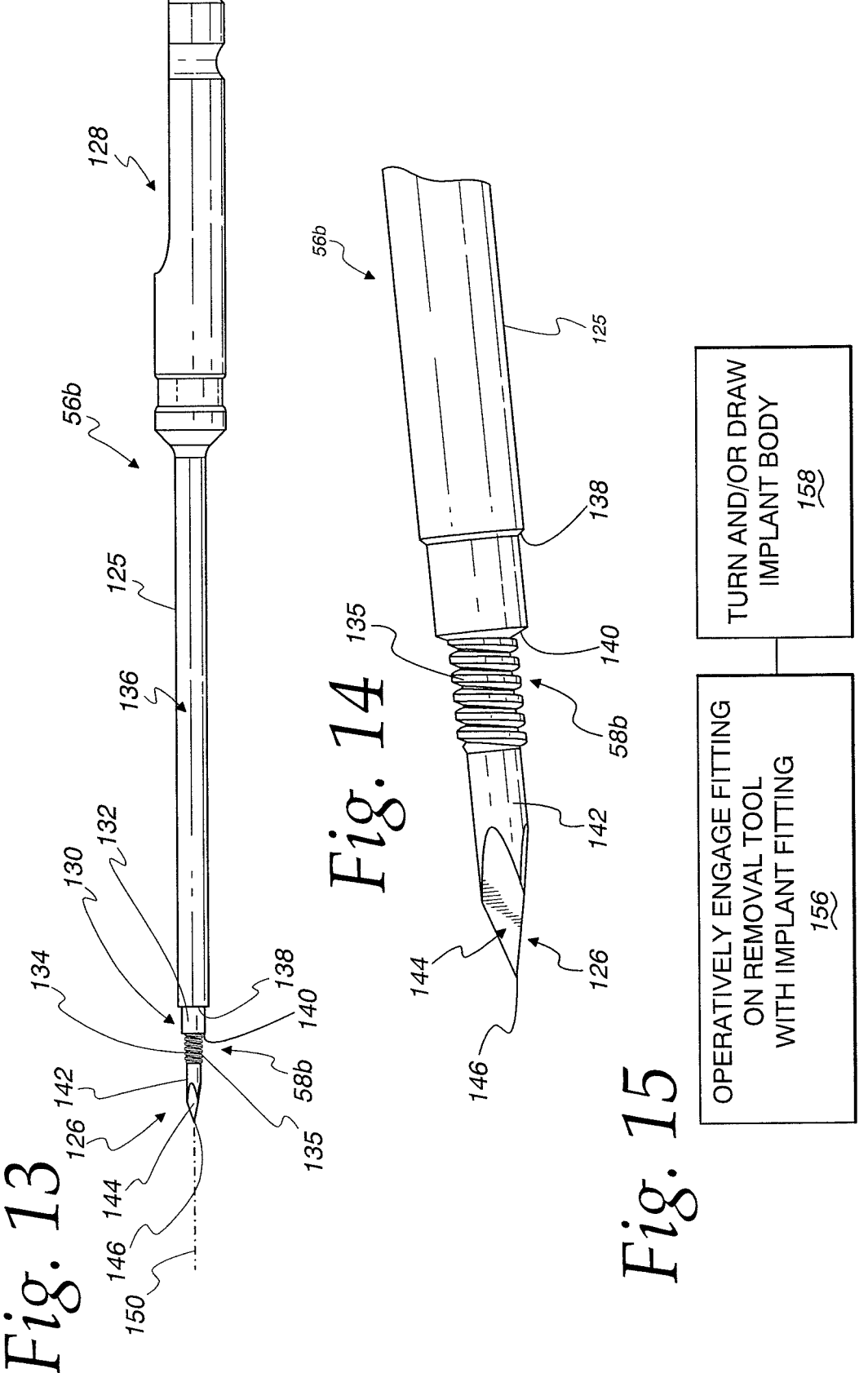
FIG. 13 is reduced, a side elevation view of the entire tool as shown in FIG. 12.
FIG. 14 is a fragmentary, perspective view of the tool in FIGS. 12 and 13.
FIG. 15 is a schematic representation of a method of controlling an implant to remove the same from an operative position, according to the invention.

According to the invention, the removal turning tool 56b, as shown in detail in FIGS. 12-14, can be utilized to effect the implant extraction. The removal turning tool 56b has the aforementioned fitting 58b that cooperates with the receptacle 82 on the turning fitting 48 and another part of the turning fitting 48 at 122, consisting of internal threads 124 extending around a portion of the through passage 64 on the body 42.

The removal turning tool 56b has an elongate shaft 125 with a leading end at 126 at which the fitting 58b is defined and a graspable handle 128 connected to the shaft 125, at an end opposite the leading end 126, that can be engaged to turn the removal tool 56b and the fitting 58b. The depicted graspable "handle" 128 may perform as a coupling for another handle component that is grasped.

The removal turning tool 56b has a stepped diameter region at 130, where the fitting 58b is defined, with a larger diameter portion at 132 that can be translated snugly into the receptacle 82, and a smaller diameter portion 134 on which external threads 135 are provided that are engageable with the threads 124 on the body 42.

A lengthwise portion 136 of the shaft 125 on the removal turning tool 56b has a substantially uniform diameter that is greater than that of the portion 132 whereby an annular shoulder 138 is defined at the transition therebetween. Another annular shoulder 140 is defined at the transition between the portions 132, 134.

The removal turning tool 56b further includes a guide portion 142 that has a region 144 that is tapered towards a sharp leading end 146 on the removal turning tool 56b.

The fitting 58b on the removal turning tool 56b operatively engages the cooperating turning fitting 48 as follows. The guide portion 142 is first introduced to the receptacle 82. The tapered region 144 of the guide portion 142 facilitates introduction of the fitting 58b into the receptacle 82 and subsequently guides movement thereof into the through passage 64, including the portion of the through passage 64 bounded by the threads 124. The guide portion 142 is dimensioned relative to the through passage 64 such that its translation within the through passage 64 aligns the external threads 135 on the smaller diameter portion 134 to be engaged with the internal threads 124 extending around the through passage 64. By then turning the fitting 58b around its axis 150, the threads 124, 135 cooperate so that the fitting 58b is advanced relative to the body 42 to the FIG. 12 position wherein the fitting 58b is operatively engaged with the cooperating turning fitting 48 on the body 42.

Turning of the fitting 58b relative to the fitting 48 is arrested by one or both of: a) the shoulder 138 engaging an edge 152 at the trailing end of the body 42; and b) the shoulder 140 engaging an axially facing edge 154 at the base of the receptacle 82. This produces a binding action between the threads 124, 135 that effectively locks the position of the fitting 58b relative to the fitting 48.

The threads 60, 62 and cooperating threads 124, 135 are opposite-handed. As depicted, the threads 60, 62 are right-handed threads, with the threads 124, 135 being left-handed threads. Accordingly, the implant 40 is advanced into its operative position by turning the body 42 in a "right-handed" direction around the axis 90.

By reason of engaging the threads 124, 135 by turning the fitting 58b in a left-handed direction around the axis 90, once the threads 124, 135 bind or are locked by reason of the inclusion of the shoulders 138, 140, continued force application in the left-handed turning direction causes the body 42 to follow this fitting movement, which is in a loosening direction for the body 42. At the same time, by reason of this locking thread/shoulder arrangement, an axial force can be applied to the turning tool 56b which allows the fitting 58b to draw the body 42 in an axial direction out of the passage 94.

Accordingly, the assembly turning tool 56a can be utilized to place the implant in its operative position. When extraction of the implant 40 is desired, the removal turning tool 56b can be used to engage the operatively positioned implant 40 and effect extraction thereof. The removal turning tool 56b thus does not rely on thread purchase between the body 42 and bone to effect extraction. The removal turning tool 56b can be operated to turn and/or apply an axial force to the operatively positioned implant 40.

It is also contemplated that the same concept can be practiced using cooperating parts that partially or fully form the required threads as the parts are engaged.

These steps are shown in flow diagram form in FIG. 15. As shown at block 156 therein, a fitting on the removal turning tool is operatively engaged with a cooperating fitting on the implant that is in an operative position with respect to bone.

As shown at block 158, the removal turning tool is operated to turn and/or draw the body axially to thereby withdraw the implant from its operative position and potentially fully separate the implant from the bone.

It should be noted that different configurations may be devised for the fittings 58b, 48 to allow the turning and/or drawing action to be imparted to the implant through removal turning tool. The form depicted is exemplary in nature only.

It is also desirable that the diameter D9 of the tool portion 136 that projects away from the trailing end 46 of the implant body 42 with the fittings 58b, 48 engaged, be less than the diameter of the root 110 over at least a length that will be required to pass through articular cartilage during a procedure, whereby damage thereto may be minimized.

While the nature of the passage 94 is not limited, the passage 94 in FIG. 12 is a medullary canal. The bone depicted schematically in FIG. 10 may be any bone, and potentially a hand or foot bone, such as a metacarpal, metatarsal, or phalangeal bone.

It should also be noted that while the removal turning tool relies upon using opposite-handed threads, it is not critical as to which handed thread is at either location. For example, while the threads 60, 62 are shown as right-handed, these threads could be left-handed, with the threads 124, 135 being right-handed.

The foregoing disclosure of specific embodiments is intended to be illustrative of the broad concepts comprehended by the invention.

The invention claimed is:

1. A method of controlling an implant with respect to a bone that is one of a metacarpal, metatarsal, and phalangeal bone of one of a foot or hand, the method comprising the steps of:

obtaining an implant having a body with a lengthwise axis, the body having a leading end and a trailing end and external threads extending around the lengthwise axis, wherein the external threads comprise first and second threaded lengths with the body having an unthreaded shank portion between the first and second threaded lengths, the first and second threaded lengths respectively having first and second roots each with a diameter, wherein the diameters of the first and second roots are approximately the same;

directing the implant through an exposed surface of the bone into a passage in the bone and turning the body in a first turning direction around the lengthwise axis to thereby cause the external threads to engage a bone surface bounding the bone passage so as to cause the implant to advance in a first assembly direction relative to the bone into an operative position, the trailing end of the implant body is one of flush with or below the exposed bone surface with the implant in the operative position;

obtaining a removal tool having a first fitting;

with the implant in the operative position, operatively engaging the first fitting with a cooperating fitting on the implant body at or adjacent to the trailing end so that the first fitting is in lengthwise overlapping relationship with the external threads at the trailing end of the implant body and can be moved to thereby: a) turn the body in a second turning direction around the lengthwise axis that is opposite to the first turning direction; and b) draw the body oppositely to the first assembly direction; and with the implant in the operative position and the first fitting engaging the cooperating fitting on the body, controlling the removal tool so as to a) turn the body in the second turning direction; and b) draw the body oppositely to the first assembly direction by exerting a force on the body oppositely to the first assembly direction through the removal tool to thereby withdraw the implant from its operative position.

2. The method of controlling an implant with respect to a bone according to claim 1 wherein the implant has an axial through passage between the leading and trailing ends of the body.

3. The method of controlling an implant with respect to a bone according to claim 2 wherein the passage in the bone is a medullary canal and the step of directing the implant into the passage comprises directing a guide pin into the medullary canal, engaging the body with the guide pin so that the guide pin extends into the axial through passage on the implant, and guiding the body along the guide pin.

4. The method of controlling an implant with respect to a bone according to claim 1 wherein the first and second threaded lengths each has threads with a pitch, and the pitch of the threads on the first threaded length is substantially the same as the pitch of the threads on the second threaded length.

5. The method of controlling an implant with respect to a bone according to claim 1 wherein the first and second threaded lengths each has threads with a pitch and the pitch of the threads on the first threaded length is different from the pitch of the threads on the second threaded length.

6. The method of controlling an implant with respect to a bone according to claim 1 wherein the step of turning the body in the first turning direction comprises turning the body through a second fitting on an assembly tool with the second fitting engaged with the body, the second fitting having an axis that aligns with the lengthwise axis of the body with the second fitting engaged with the body, the body and second fitting configured so that with the second fitting engaged with the body the second fitting and body overlap axially relative to the second fitting axis and lengthwise body axis.

7. The method of controlling an implant with respect to a bone according to claim 6 wherein the second fitting has a peripheral surface extending around the axis of the second fitting and an axial length of the peripheral surface of the second fitting extending away from the body with the second fitting engaged with the body has a diameter less than or equal to a diameter of the unthreaded shank portion.

8. The method of controlling an implant with respect to a bone according to claim 6 wherein the second fitting has a peripheral surface extending around the axis of the second fitting, the trailing end of the implant has an outer diameter, and an axial length of the peripheral surface of the second fitting extending away from the body with the second fitting engaged with the body has a diameter less than or equal to the outer diameter of the trailing end of the body.

9. The method of controlling an implant with respect to a bone according to claim 8 wherein the bone passage is a medullary canal and the bone has articular cartilage with a thickness thereon and the step of directing the implant into the bone passage comprises directing the implant through the thickness of the articular cartilage, and the axial length of the peripheral surface of the second fitting is at least equal to the thickness of the articular cartilage.

10. The method of controlling an implant with respect to a bone according to claim 6 wherein the second fitting has a peripheral surface extending around the axis of the second fitting, the external threads extend from a root portion with a diameter, and a part of the second fitting that is axially overlapped with the body has a diameter that is less than or equal to the diameter of the root portion.

11. The method of controlling an implant with respect to a bone according to claim 6 wherein the body has an axially extending receptacle into which the second fitting is directed with the second fitting engaged with the body.

12. The method of controlling an implant with respect to a bone according to claim 11 wherein the first fitting has threads that engage threads on the body, and the threads on the body extend axially towards the leading end of the body to beyond the axially extending receptacle into which the second fitting is directed.

13. The method of controlling an implant with respect to a bone according to claim 12 wherein the axially extending receptacle has a diameter that is greater than a diameter of a portion of an axial through passage that is surrounded by the threads on the body that engage the threads on the first fitting.

14. The method of controlling an implant with respect to a bone according to claim 1 wherein the root on the first threaded length has first threads with a crest diameter, the root on the second threaded length has second threads with a crest diameter, and at least a portion of the second threads has a crest diameter greater than a crest diameter of at least a portion of the first threads.

15. The method of controlling an implant with respect to a bone according to claim 1 wherein the removal tool has a leading end and a graspable handle spaced from the leading end that can be engaged to turn the removal tool and the first fitting, and the removal tool has a tapered guide portion that extends to beyond the threads on the first fitting towards the leading end.

16. The method of controlling an implant with respect to a bone according to claim 1 wherein with the implant in the operative position, the trailing end of the body is recessed below the external surface of the bone.

17. The method of controlling an implant with respect to a bone according to claim 1 wherein the exposed surface of the bone is at a joint.

18. The method of controlling an implant with respect to a bone according to claim 17 wherein there is articular cartilage at the exposed surface of the bone through which the implant is directed.

19. A method of controlling an implant with respect to a bone that is one of a metacarpal, metatarsal, and phalangeal bone of a foot or hand, the method comprising the steps of:

obtaining:

a) an implant comprising:

a body with a lengthwise axis, the body having a leading end and a trailing end and external threads extending around the lengthwise axis, the external threads extending around the lengthwise axis of the body at or adjacent each of the leading end and trailing end of the body with a length portion of the body unthreaded between the leading and trailing ends of the body, the body having a shank portion with a diameter and an axial through passage between the leading and trailing ends of the body, the body further having a receptacle with threads extending around the receptacle; and b) a removal tool with a length and a first fitting having threads, the threads around the receptacle on the body spaced from the trailing end of the implant body;

directing the body in an assembly direction through an exposed surface on the bone into a passage in the bone at an articular joint and turning the body in a first direction around the lengthwise axis to cause the external threads on the body to engage a bone surface bounding the passage to thereby advance the implant into an operative position wherein the trailing end of the implant is one of flush with or below the exposed bone surface; and with the implant in the operative position, engaging the threads on the removal tool with the threads around the receptacle so that the body follows movement of the first fitting as the first fitting is: a) turned in a direction opposite to the first direction; and b) drawn in a direction oppositely to the assembly direction to thereby allow the implant to be separated from the bone, wherein the removal tool has a leading end that is directed into the receptacle to guide the threads on the first fitting up to the threads on the body for engagement with the threads on the body.

20. The method of controlling an implant with respect to a bone according to claim 19 wherein with the first fitting engaged with the body the first fitting overlaps the body over a first axial length and the first fitting has an axial length: a) extending away from the trailing end of the implant body that is at least equal to the first axial length; and b) having a diameter that is less than or equal to the diameter of the body shank portion.

21. The method of controlling an implant with respect to a bone according to claim 19 wherein with the first fitting engaged with the body the first fitting overlaps the body over a first axial length and the first fitting has an axial length: a) extending away from the trailing end of the body that is at least equal to the first axial length; and b) having a diameter that is less than or equal to a diameter of a root away from which the external threads project.

22. A method of controlling an implant with respect to a bone that is one of a metacarpal, metatarsal, and phalangeal bone of a foot or hand, the method comprising the steps of:

obtaining an implant having a body with a lengthwise axis, the body having a leading end and a trailing end and external threads extending around the lengthwise axis at or adjacent the leading end and the trailing end of the body with a length portion of the body unthreaded between the leading and trailing end of the body;

directing the implant through an exposed surface of the bone at an articular joint into a passage in the bone and turning the body in a first turning direction around the lengthwise axis to thereby cause the external threads to engage a bone surface bounding the bone passage so as to cause the implant to advance in a first assembly direction relative to the bone into an operative position, the trailing end of the implant body is one of flush with or below the exposed bone surface with the implant in the operative position;

obtaining a removal tool having a first fitting;

with the implant in the operative position, operatively engaging the first fitting with a cooperating fitting on the body at or adjacent to the trailing end so that the first fitting can be moved to thereby: a) turn the body in a second turning direction around the lengthwise axis that is opposite to the first turning direction; and b) draw the body oppositely to the first assembly direction; and with the implant in the operative position and the first fitting engaging the cooperating fitting on the body, controlling the removal tool to: a) turn the body in the second turning direction; and b) draw the body oppositely to the first assembly direction to thereby withdraw the implant from its operative position, wherein the first fitting has threads that engage threads on the cooperating fitting on the body, wherein the external threads and the threads on the first fitting are opposite-handed, wherein the step of operatively engaging the first fitting comprises turning the first fitting relative to the body around the lengthwise axis in the second turning direction, wherein the removal tool has a stepped diameter region adjacent a leading end of the removal tool with a first diameter portion and a second diameter portion is projected into an axially extending receptacle on the body, wherein the stepped diameter region has an annular shoulder facing in one direction which abuts to an oppositely facing edge on the body with the first fitting fully operatively engaged with the body, whereby with the first fitting fully engaged with the body, the first fitting is blocked from further turning relative to the body in the second turning direction and the threads on the first fitting bind, and thereby become locked, with the threads on the cooperating fitting on the body so that a part of the body is fixedly held between the threads on the first fitting and the annular shoulder facing in the one direction.

* * * * *